(12) United States Patent
Li

(10) Patent No.: US 9,421,295 B1
(45) Date of Patent: Aug. 23, 2016

(54) AROMA DIFFUSER WITH ADJUSTABLE ESSENTIAL OIL GAS PROPORTION AND AROMA DIFFUSING METHOD

(71) Applicant: Puzhen Life Co., Limited, Hong Kong (HK)

(72) Inventor: Dong Sheng Li, Hong Kong (HK)

(73) Assignee: PUZHEN LIFE CO., LIMITED, Hong Kong (HK)

( * ) Notice: Subject to any disclaimer, the term of this patent is extended or adjusted under 35 U.S.C. 154(b) by 0 days.

(21) Appl. No.: 15/065,893

(22) Filed: Mar. 10, 2016

(30) Foreign Application Priority Data

Feb. 18, 2016 (CN) .......................... 2016 1 0092112

(51) Int. Cl.
| | |
|---|---|
| *A61L 9/14* | (2006.01) |
| *A61M 11/02* | (2006.01) |
| *A61M 11/06* | (2006.01) |
| *B05B 7/00* | (2006.01) |
| *A61L 9/12* | (2006.01) |

(52) U.S. Cl.
CPC ...... *A61L 9/14* (2013.01); *A61L 9/12* (2013.01); *A61L 9/125* (2013.01); *A61M 11/02* (2013.01); *A61M 11/06* (2013.01); *B05B 7/0012* (2013.01)

(58) Field of Classification Search
CPC ........ A61L 9/14; A61M 11/00; A61M 11/02; A61M 11/06; B05B 7/0012; B05B 7/2405; B05B 7/2416; B05B 7/2472
See application file for complete search history.

(56) References Cited

U.S. PATENT DOCUMENTS

| | | | | |
|---|---|---|---|---|
| 2,826,454 A | * | 3/1958 | Coanda | A61M 11/06 128/200.18 |
| 6,405,944 B1 | * | 6/2002 | Benalikhoudja | A61L 9/145 128/200.18 |
| 9,211,357 B1 | * | 12/2015 | Li | A61L 9/14 |
| 9,358,557 B2 | * | 6/2016 | Young | B05B 7/0012 |
| 2002/0068023 A1 | * | 6/2002 | Davis | A61L 9/12 422/124 |
| 2010/0084484 A1 | * | 4/2010 | Sevy | A61M 11/06 239/4 |
| 2010/0326117 A1 | * | 12/2010 | Hipp | A61L 9/015 62/292 |
| 2012/0018530 A1 | * | 1/2012 | Blaylock | A61L 9/122 239/7 |

FOREIGN PATENT DOCUMENTS

| | | |
|---|---|---|
| CN | 101107036 A | 1/2008 |
| CN | 204072864 U | 1/2015 |

OTHER PUBLICATIONS

Search Report issued by the Chinese Patent Office on Apr. 22, 2016.

* cited by examiner

*Primary Examiner* — Ryan Reis

(57) ABSTRACT

The present invention relates to an aroma diffuser with an adjustable essential oil gas proportion and an aroma diffusing method. The aroma diffuser includes a housing, an electric control element, at least two essential oil bottles, gasification elements corresponding to the essential oil bottles, pump elements corresponding to the gasification elements and a fragrance mixing element. The lower end of each of the gasification elements is connected to an open end of the corresponding essential oil bottle. Each of the gasification elements communicates with the open end of the corresponding essential oil bottle. An upper end of each of the gasification elements stretches into a cavity at the lower end of the fragrance mixing element and fits with the end face of the cavity. The present invention features a compact structure, high sealing performance, easy assembly and simple operation.

21 Claims, 7 Drawing Sheets

AROMA DIFFUSER WITH ADJUSTABLE ESSENTIAL OIL GAS PROPORTION AND AROMA DIFFUSING METHOD

CROSS-REFERENCE TO RELATED APPLICATIONS

The present application claims the benefit of Chinese Patent Application No. 201610092112.3 filed on Feb. 18, 2016, the contents of which are hereby incorporated by reference.

TECHNICAL FIELD

The present invention relates to an aroma diffuser, particularly to an aroma diffuser with an adjustable essential oil gas proportion and an aroma diffusing method.

DESCRIPTION OF THE BACKGROUND

Aroma diffusers make use of the unique charm of fragrance and extend communication from vision and hearing to smell and even deeper layers.

Following the improvement of people's living standard, more and more people use essential oil to relieve nerves, preserve life, ease tension or soothe the mind. In general, essential oil is classified into single essential oil and compound essential oil. Single essential oil is the essence extracted from a whole plant or a specific location of the plant and typically has rich odor of this plant, a specific efficacy and individual features. Compound essential oil is a mixture of two or more than two essential oils in order to achieve a specific curative effect. These essential oils are mutually coordinated and supplement each other to boost the curative effect. Conventional aroma diffusers allow addition of only one kind of single essential oil or readymade compound essential oil and don't have the function of blending compound essential oil gases. The compound essential oil has to be bought from the market. The use is inconvenient. Normally they cannot meet people's usage requirements.

Therefore, it is in urgent need of an aroma diffuser with an adjustable essential oil gas proportion.

SUMMARY OF THE INVENTION

The object of the present invention is to overcome the shortcoming of the prior art and provide an aroma diffuser with an adjustable essential oil gas proportion and an aroma diffusing method. Through adjusting the proportion of the essential oil gases, a compound essential oil gas that meets people's usage requirements can be obtained through blending.

The object of the present invention is realized in the following way. The aroma diffuser with an adjustable essential oil gas proportion provided by the present invention comprises a housing and an electric control element on the housing. It has the following improvements: inside the housing there are at least two essential oil bottles, gasification elements corresponding to the essential oil bottles, pump elements corresponding to the gasification elements and a fragrance mixing element. The lower end of each of the gasification elements is connected to an open end of the corresponding essential oil bottle. Each of the gasification elements communicates with the open end of the corresponding essential oil bottle. The upper end of each of the gasification elements stretches into a cavity at the lower end of the fragrance mixing element and fits with the end face of the cavity. The lower end of the fragrance mixing element communicates with the upper end of each of the gasification elements. The upper end of the fragrance mixing element communicates with a centralized fragrance diffusion outlet. Each of the pump elements is connected to the corresponding gasification element and the electric control element. Each of the pump elements communicates with the corresponding gasification element.

Further, inside the housing there is a support plate. The support plate comprises first grooves corresponding to all the gasification elements. The gasification elements are placed inside the first grooves. The bottom surfaces of the first grooves comprise second grooves, and the essential oil bottles connected to the lower ends of the gasification elements are placed inside the second grooves.

Further, each of the gasification elements comprises a gasification chamber body. The lower end of the gasification chamber body is connected to the open end of the corresponding essential oil bottle. The gasification chamber body comprises a gasification chamber, an air chamber, and an essential oil nozzle, an air inlet and an oil conduit disposed at the lower end of the gasification chamber body. The gasification chamber communicates with the air chamber through an air nozzle. The upper end of the essential oil nozzle stretches into the gasification chamber and is close to the air nozzle. The gasification chamber communicates with the essential oil nozzle and the open end of the corresponding essential oil bottle respectively. The air inlet communicates with the air chamber. The oil conduit is disposed at the lower end of the essential oil nozzle. The oil conduit communicates with the essential oil nozzle. The lower end of the oil conduit stretches into the corresponding essential oil bottle. The surface of the lower end of the oil conduit is close to the bottom surface of the essential oil bottle, and is a slope.

Further, each of the gasification elements further comprises a gasification chamber cover. The gasification chamber cover is snapped into the gasification chamber body. The upper end of the gasification chamber cover stretches into the cavity at the lower end of the fragrance mixing element and fits with the end face of the cavity. The upper end of the gasification chamber cover comprises a fragrance outlet. The fragrance outlet communicates with the gasification chamber and the fragrance mixing element respectively.

Further, the fragrance mixing element comprises a mixing chamber cover, a mixing blade and a mixing chamber base. The mixing chamber cover is snapped into the mixing chamber base. The mixing blade is snapped into the mixing chamber base and contained in a mixing chamber enclosed by the mixing chamber cover and the mixing chamber base. The mixing chamber base is disposed on the support plate. The upper end of the mixing chamber cover comprises a fragrance converging port, inlaid in the centralized fragrance diffusion outlet at the upper end of the housing. The fragrance converging port communicates with the centralized fragrance diffusion outlet and the mixing chamber respectively. The upper end of the mixing chamber base comprises fragrance access passages corresponding to each of the gasification elements. The fragrance access passages communicate with the mixing chamber. The lower end of the mixing chamber base has a cavity, enclosing the first groove to underneath of the cavity. The upper end of the gasification chamber cover stretches into the cavity and fits with the end face of the cavity. The fragrance inlet communicates with the fragrance outlet. The fragrance access passage is on the end face of the cavity.

Further, each of the pump elements comprises a pump mounting rack disposed inside the housing, a pump body disposed inside the pump mounting rack, an air duct, a holder and an air output nozzle. The holder is disposed on the lower end of the first groove receiving the corresponding gasification element. The holder comprises a mounting hole. One end of the air duct is connected to the pump body. Another end of the air duct sticks out from an upper end of the pump mounting rack and is fixed onto the mounting hole. The air duct communicates with the mounting hole. The lower end of the air output nozzle is fixed onto the mounting hole. The upper end of the air output nozzle passes through the first groove, is inlaid in the air inlet and stretches into the air chamber. The air output nozzle communicates with the air chamber and the mounting hole respectively.

Further, the gasification chamber body further comprises a lower vortex body and an upper vortex body. The lower vortex body and the upper vortex body are disposed inside the gasification chamber from bottom to top in turn. The lower end of the upper vortex body is connected to the lower vortex body. The upper end of the upper vortex body is connected to the gasification chamber cover. The upper vortex body, the lower vortex body and the gasification chamber are mutually communicable.

Further, the electric control element comprises a control panel, a pump flow regulating button corresponding to each pump element, a time setting button and a power switch. The pump flow regulating button, the time setting button and the power switch are all connected to the control panel The control panel is connected to all pump elements.

Further, the gasification chamber body further comprises a pressure plunger. The pressure plunger is disposed on a side face of the gasification chamber body. One end of the pressure plunger is inside the air chamber. The position of the pressure plunger corresponds to the position of the air nozzle.

Further, bottom surface of the gasification chamber comprises an annular flange inlaid in the open end of the corresponding essential oil bottle.

Further, an O ring is disposed between the annular flange and the corresponding essential oil bottle.

Further, the lower end of the gasification chamber body comprises a first thread. The open end of the corresponding essential oil bottle comprises a corresponding second thread. The first thread is connected to the second thread.

Further, a seal ring is disposed between the oil conduit and the lower end of the essential oil nozzle.

Further, a pump cover is disposed at the lower end of the pump mounting rack.

Further, the upper end of the gasification chamber cover comprises a cover groove. The bottom surface of the cover groove comprises a fragrance outlet. The fragrance outlet fits with the lower end of the fragrance inlet and communicates with the gasification chamber and the fragrance inlet respectively.

The present invention further provides an aroma diffusing method, comprising: providing an aroma diffuser comprising: a housing, at least two essential oil bottles, gasification elements, pump elements, a fragrance mixing element and an electric control element; under action of the electric control element, importing ambient air into air chambers of the gasification elements through pump bodies of the pump elements and forming jet stream; spraying the jet stream above an essential oil nozzle of each of the gasification elements to form negative pressure so as to suck liquid essential oil out from the respective essential oil bottles and gasify the liquid essential oil into essential oil gas; mixing the essential oil gas, and diffusing the mixed essential oil gas to ambient air through a centralized fragrance diffusion outlet of the housing.

The aroma diffusing method further comprises regulating flow and working time of each pump body of the pump elements according to actual need to achieve the required essential oil mixing proportion and working time.

The aroma diffusing method further comprises: collecting the essential oil gas which becomes liquid essential oil when it collides with inner walls of the gasification chambers of the respective gasification elements back to the respective essential oil bottles.

Further, the fragrance mixing element comprises a mixing blade with a spiral channel. The gasified essential oil gases rotate and are mixed in the spiral channel after the gasified essential oil gases are imported to the mixing chamber of the fragrance mixing element.

The aroma diffusing method further comprises: forming the gasified essential oil gases into vortex airstreams through lower vortex bodies and upper vortex bodies of the gasification elements and importing the airstreams into the mixing chamber of the fragrance mixing element for mixing.

Further, the upper vortex bodies and the lower vortex bodies form spiral channels. When essential oil gases pass the spiral channels, the essential oil gases in large particle size are blocked, flow back into the gasification chambers and return to the essential oil bottles along inner walls of the gasification chambers, while the essential oil gases in small particle size are imported to the mixing chamber of the fragrance mixing element for mixing.

Compared with the prior art, the present invention has the following beneficial effect: through the provided gasification elements corresponding to the essential oil bottles, the pump elements corresponding to the gasification elements, and the fragrance mixing element, the present invention may adjust the mixing proportions of different essential oils, obtain an essential oil gas mixed according to the proportion, achieve the effect of mixed compound essential oil and meet people's usage requirements. The present invention features a compact structure, high sealing performance, easy assembly and simple operation.

Where: 1, housing; 2, essential oil bottle; 3, centralized fragrance diffusion outlet; 4, gasification chamber body; 5, gasification chamber; 6, air chamber; 7, essential oil nozzle; 8, oil conduit; 9, air nozzle; 10, gasification chamber cover; 11, cavity; 12, fragrance outlet; 13, mixing chamber cover; 14, mixing blade; 15, mixing chamber base; 16, fragrance converging port; 17, fragrance access passage; 18, fragrance inlet; 19, pump mounting rack; 20, pump body; 21, air duct; 22, holder; 23, air output nozzle; 24, mounting hole; 25, support plate; 26, first groove; 27, second groove; 28, lower vortex body; 29, upper vortex body; 30, pressure plunger; 31, annular flange; 32, O ring; 33, pump cover; 34, cover groove; 35, control panel; 36, pump flow regulating button; 37, time setting button; 38, power switch; 39, air inlet.

DETAILED DESCRIPTION OF PREFERRED EMBODIMENTS

Below the present invention will be further described by referring to the accompanying drawings and embodiments.

Figure 1:
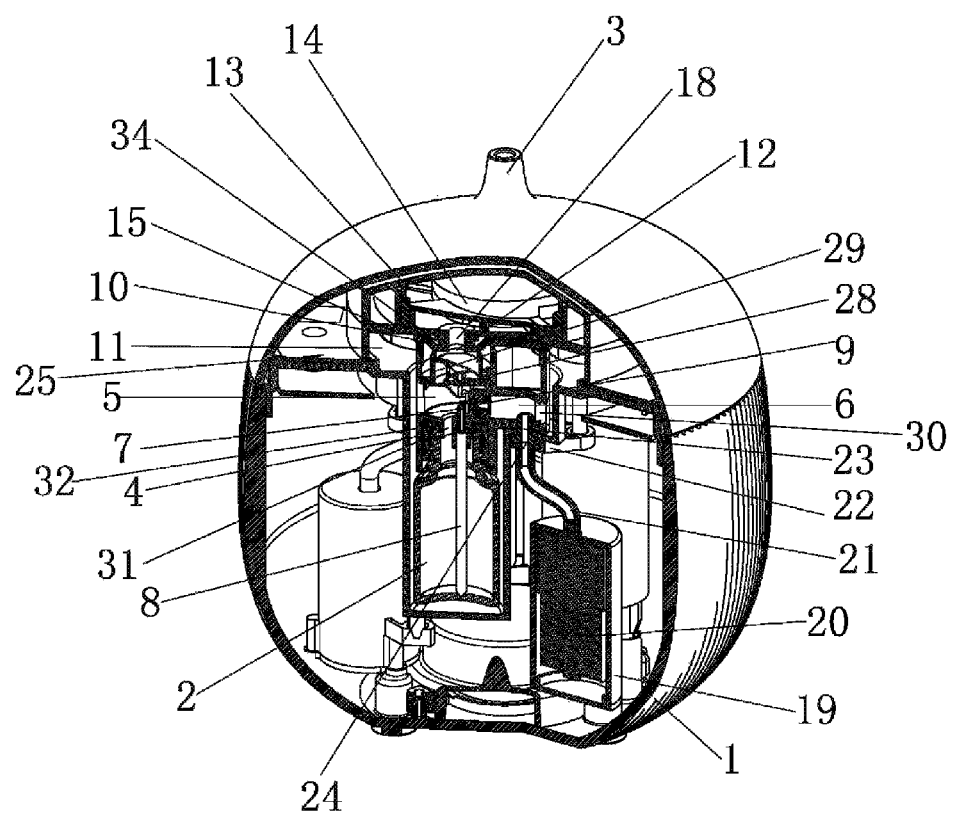
FIG. 1 is a structural schematic of an aroma diffuser with an adjustable essential oil gas proportion provided by the present invention.
Figure 2:
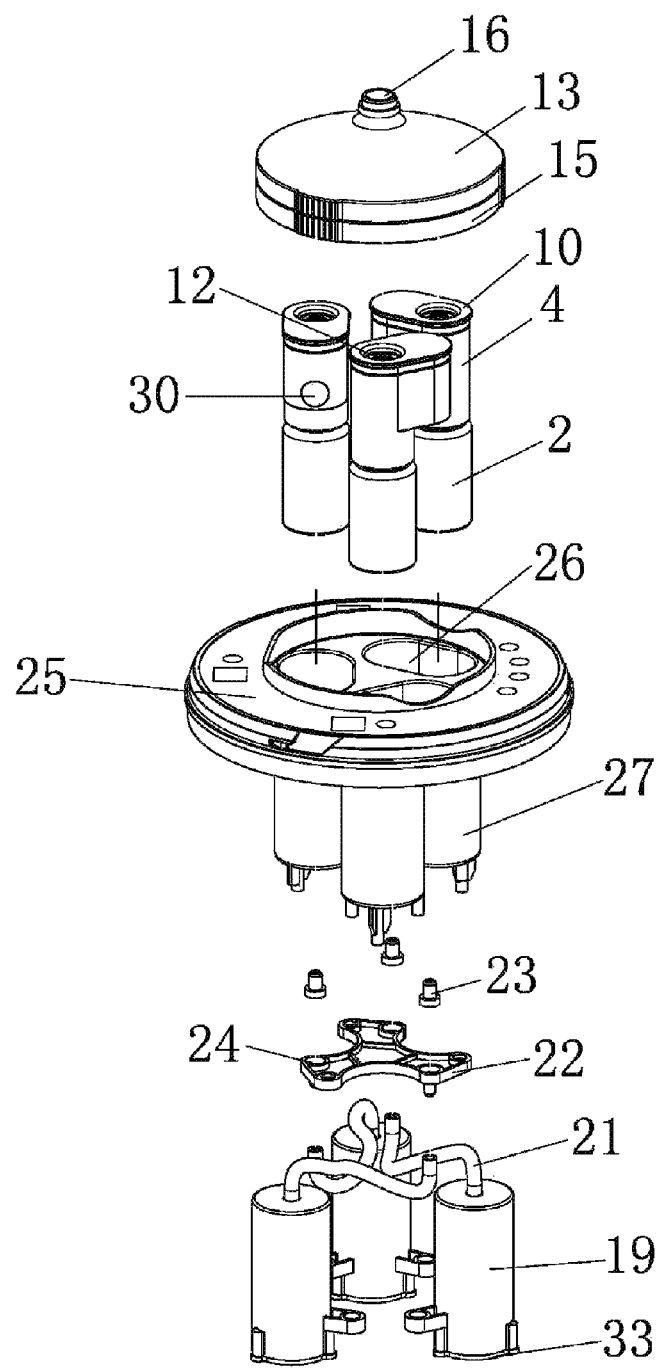
FIG. 2 is an internal structural schematic of an aroma diffuser with an adjustable essential oil gas proportion provided by the present invention.

As shown in FIG. 1 and FIG. 2, the present invention discloses an aroma diffuser with an adjustable essential oil gas proportion, comprising a housing 1 and an electric control element on the housing 1. In this embodiment, the electric control element is disposed on a side face of the housing 1, and inside the housing 1 there are at least two essential oil bottles 2, gasification elements corresponding to the essential oil bottles 2, pump elements corresponding to the gasification elements and a fragrance mixing element. To be specific, the quantity of the gasification elements is same as the quantity of the essential oil bottles 2, and the quantity of the pump elements are same as the quantity of the gasification elements. The lower end of each of the gasification elements is connected to an open end of the corresponding essential oil bottle 2, each of the gasification elements communicates with the open end of the corresponding essential oil bottle 2, and the upper end of each of the gasification elements stretches into the cavity 11 at the lower end of the fragrance mixing element and fits with an end face of the cavity 11. The lower end of the fragrance mixing element communicates with the upper end of each of the gasification elements, and the upper end of the fragrance mixing element communicates with a centralized fragrance diffusion outlet 3 at the upper end of the housing 1. Each of the pump elements is connected to the corresponding gasification element and the electric control element, and each of the pump elements communicates with the corresponding gasification element. In this embodiment, as shown in FIG. 1, the housing 1 is approximately in a round shape, and certainly may be in other shapes, too.

In this embodiment, as shown in FIG. 1 and FIG. 2, inside the housing 1 there is a support plate 25. The support plate 25 comprises first grooves 26 corresponding to all gasification elements. The gasification elements are placed in the first grooves 26. The bottom surfaces of the first grooves 26 comprise second grooves 27. The essential oil bottles 2 connected to the lower ends of the gasification elements are placed inside the second grooves 27, which are for receiving the gasification elements and the essential oil bottles 2. The structure is compact.

Figure 3:
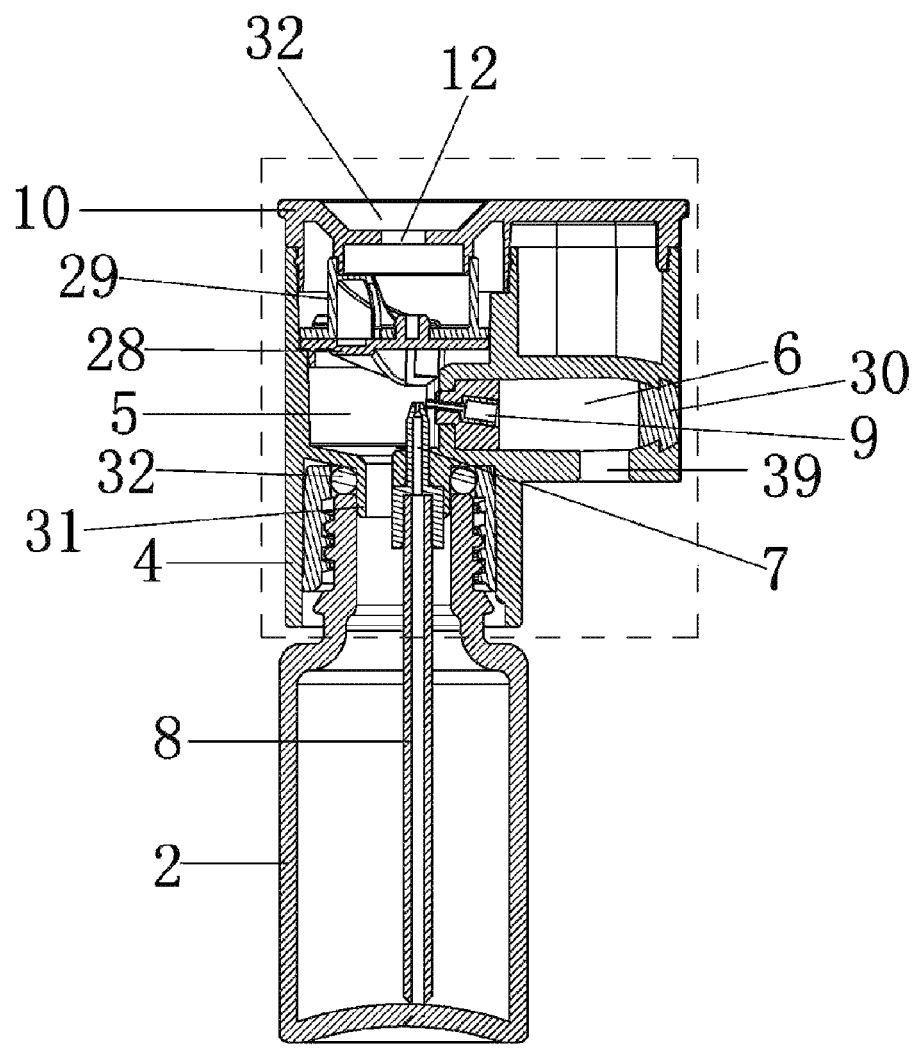
FIG. 3 is a structural schematic of the connection between a gasification element and the corresponding essential oil bottle in the present invention.

As shown in FIG. 3, the gasification element comprises a gasification chamber body 4. The lower end of the gasification chamber body 4 is connected to an open end of the corresponding essential oil bottle 2. The gasification chamber body 4 comprises a gasification chamber 5, an air chamber 6, and an essential oil nozzle 7, an air inlet 39 and an oil conduit 8 disposed at the lower end of the gasification chamber body 4. The gasification chamber 5 and the air chamber 6 are connected through an air nozzle 9. The upper end of the essential oil nozzle 7 stretches into the gasification chamber 5 and is close to the air nozzle 9. The gasification chamber 5 communicates with the essential oil nozzle 7 and an open end of the corresponding essential oil bottle 2 respectively. The air inlet 39 communicates with the air chamber 6. The oil conduit 8 is disposed at the lower end of the essential oil nozzle 7. The oil conduit 8 communicates with the essential oil nozzle 7. The lower end of the oil conduit 8 stretches into the corresponding essential oil bottle 2. The surface of the lower end of the oil conduit 8 is close to the bottom surface of the essential oil bottle 2 and is a slope. It makes for the suction of liquid essential oil and may avoid the surface of the lower end of the oil conduit 8 touching the bottom surface of the essential oil bottle 2 and obstructing the oil way. In this case, when airstream passes the air nozzle 9 and is sprayed out at a high speed, negative pressure will be formed above the essential oil nozzle 7. As a result, the oil conduit 8 will suck the liquid essential oil out from the essential oil bottle 2 and spray it to the gasification chamber 5 via the essential oil nozzle 7. Meanwhile, the jet stream sprayed from the air nozzle 9 will gasify the essential oil sprayed from the essential oil nozzle 7 into tiny particles, which will become essential oil gas.

The gasification element further comprises a gasification chamber cover 10. The gasification chamber cover 10 is snapped into the gasification chamber body 4. The upper end of the gasification chamber cover 10 stretches into a cavity 11 at the lower end of the fragrance mixing element and fits with an end face of the cavity 11. The upper end of the gasification chamber cover 10 comprises a fragrance outlet 12. The fragrance outlet 12 communicates with the gasification chamber 5 and the fragrance mixing element respectively.

Figure 4:
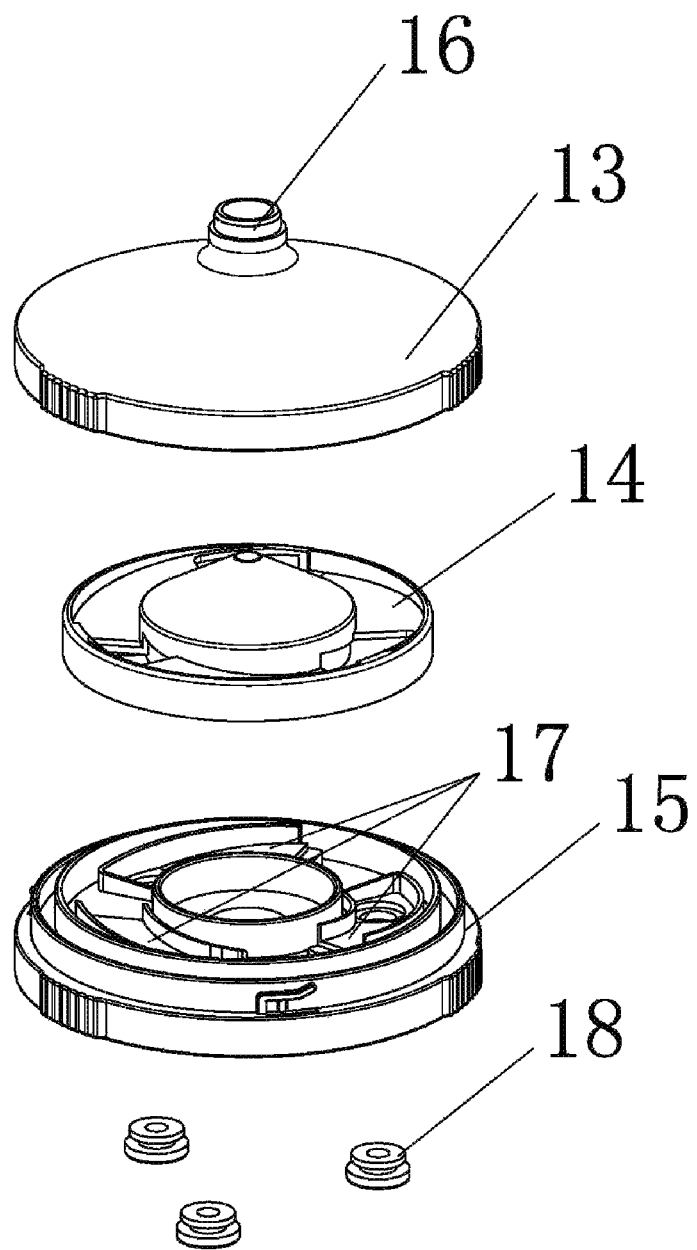
FIG. 4 is an exploded schematic of a fragrance mixing element in the present invention.

As shown in FIG. 4, the fragrance mixing element comprises a mixing chamber cover 13, a mixing blade 14 and a mixing chamber base 15. The mixing chamber cover 13 is snapped into the mixing chamber base 15. The mixing blade 14 is snapped into the mixing chamber base 15 and received in the mixing chamber enclosed by the mixing chamber cover 13 and the mixing chamber base 15. The mixing chamber base 15 is disposed on the support plate 25. The upper end of the mixing chamber cover 13 comprises a fragrance converging port 16 and is inlaid in the centralized fragrance diffusion outlet 3 at the upper end of the housing 1. The fragrance converging port 16 communicates with the centralized fragrance diffusion outlet 3 and the mixing chamber respectively. The upper end of the mixing chamber base 15 comprises fragrance access passages 17 corresponding to the gasification elements. Specifically, the quantity of the fragrance access passages 17 is equal to the quantity of the gasification elements. The fragrance access passages 17 communicate with the mixing chamber. The lower end of the mixing chamber base 15 comprises a cavity 11, enclosing the first groove 26 to underneath of the cavity. The upper end of the gasification chamber cover 10 stretches into the cavity 11 and fits with an end face of the cavity 11. The end face of the cavity 11 comprises a fragrance inlet 18 communicating with the fragrance outlet 12 and the fragrance access passage 17 respectively. The fragrance inlet 15 corresponds to the fragrance outlet 12 and fragrance access passage 17. The essential oil gas discharged from the fragrance outlet 12 enters the fragrance access passage 17 via the fragrance inlet 18. When the essential oil gas in the fragrance access passage 17 arrives at the inside of the mixing chamber, it rotates and is mixed in the spiral channel of the mixing blade 14. After mixing, it is diffused to the air from the centralized fragrance diffusion outlet 3 via the fragrance converging port 16, thereby achieving the effect of mixed compound essential oil.

Figure 5:
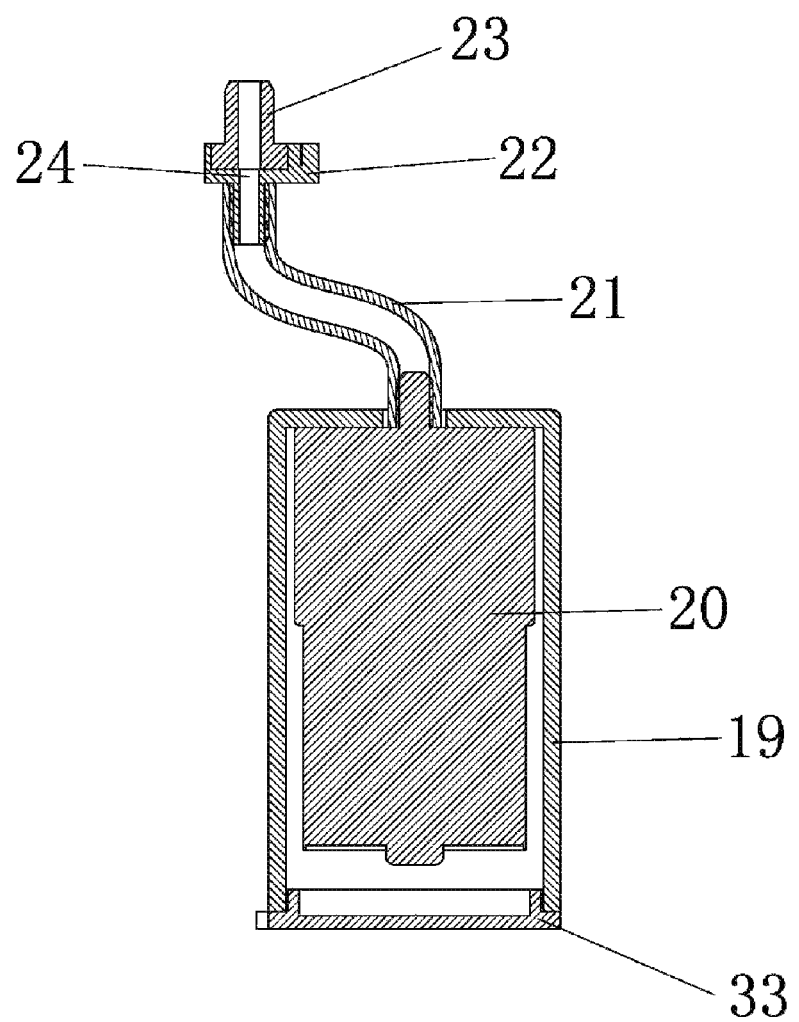
FIG. 5 is a structural schematic of a pump element in the present invention.
Figure 6:
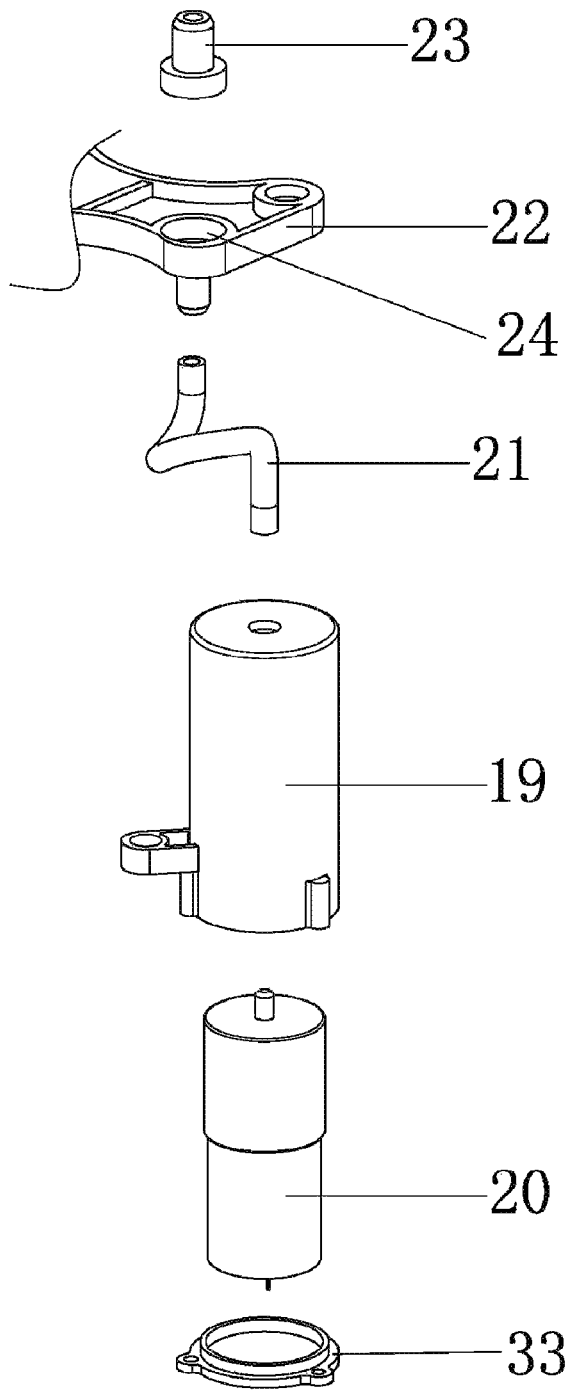
FIG. 6 is an exploded schematic of a pump element in the present invention.

As shown in FIG. 5 and FIG. 6, the pump element comprises a pump mounting rack 19 received in the housing 1, and a pump body 20, an air duct 21, a holder 22 and an air output nozzle 23 received in the pump mounting rack 19. In this embodiment, the pump mounting rack 19 is disposed on the bottom surface of the housing 1. The holder 22 is disposed on the lower end of the first groove 26 of the corresponding gasification element and there is a mounting hole 24 on the holder 22. The structure is stable and well fixed. One end of the air duct 21 is connected to the pump body 20 and another end of the air duct sticks out from an upper end of the pump mounting rack 19 and is fixed onto the mounting hole 24. The air duct 21 is connected to the mounting hole 24. The lower end of the air output nozzle 23 is fixed onto the mounting hole 24. The upper end of the air output nozzle 23 passes through the first groove 26, is inlaid in the air inlet 39 and stretches into the air chamber 6. The air output nozzle 23 communicates with the air chamber 6 and the mounting hole 24 respectively. Through this structure, the airstream output by the pump body 20 enters the air chamber 6 via the air duct 21, the mounting hole 24 and the air output nozzle 23.

In this embodiment, as shown in FIG. 1 and FIG. 3, the gasification chamber body 4 further comprises a lower vortex body 28 and an upper vortex body 29. The lower vortex body 28 and the upper vortex body 29 are disposed inside the gasification chamber 5 from bottom to top in turn. The lower end of the upper vortex body 29 is connected to the lower vortex body 28. The upper end of the upper vortex body 29 is connected to the gasification chamber cover 10. The upper vortex body 29, the lower vortex body 28 and the gasification chamber 5 are mutually communicable. The gasified essential oil gas particles form a vortex airstream under action of the lower vortex body 28 and the upper vortex body 29 to make for discharge from the fragrance outlet 12.

Figure 7:
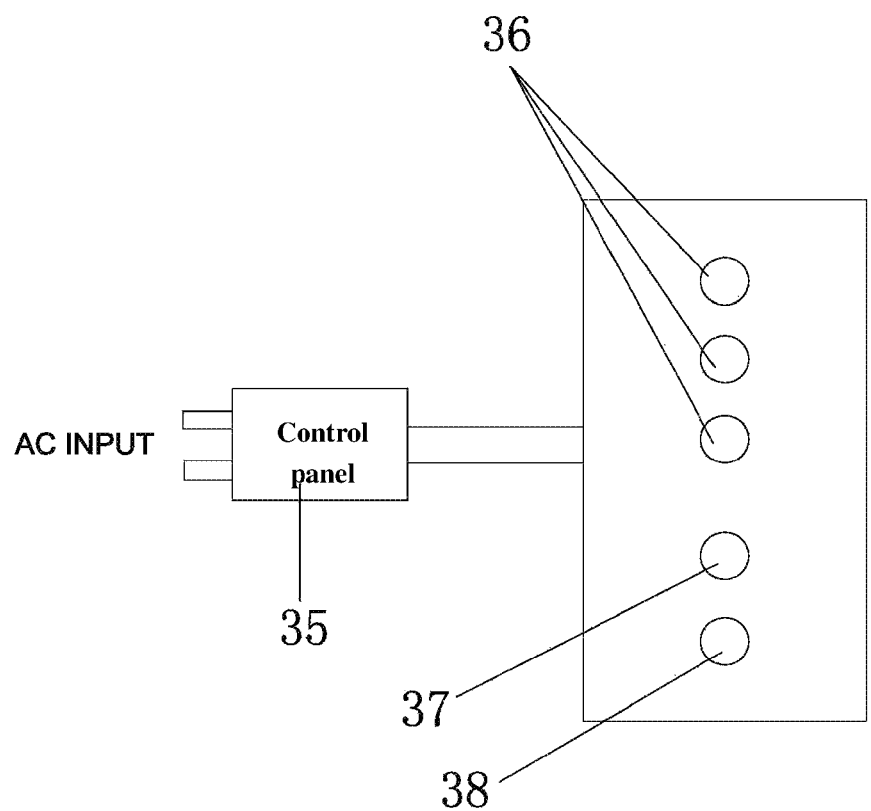
FIG. 7 is a structural schematic of an electric control element in the present invention.

In this embodiment, as shown in FIG. 7, the electric control element comprises a control panel 35, a pump flow regulating button corresponding to each pump element 36, a time setting button 37 and a power switch 38. The pump flow regulating button 36 is used to regulate the outputted gas flow so as to suck out a corresponding amount of liquid essential oil. The time setting button 37 is used to set working time. The pump flow regulating button 36, the time setting button 37 and the power switch 38 are all connected to the control panel 35. The control panel 35 is connected to all pump elements.

In this embodiment, as shown in FIG. 1 and FIG. 3, the gasification chamber body 4 further comprises a pressure plunger 30. The pressure plunger 30 is disposed on a side face of the gasification chamber body 4 and one end of the pressure plunger 30 is inside the air chamber 6. The position of the pressure plunger 30 corresponds to the position of the air nozzle 9. The pressure plunger 30 can help the air in the air chamber 6 spray out from the air nozzle 9 at a high speed.

In this embodiment, as shown in FIG. 1 and FIG. 3, there is an annular flange 31 on bottom surface of the gasification chamber 5. The annular flange 31 is inlaid in the open end of the corresponding essential oil bottle 2 so that the gasification chamber 5 communicates with the open end of the essential oil bottle 2 and the partial essential oil gas becoming liquid essential oil when it collides with the inner wall of the gasification chamber 5 can flow back to the essential oil bottle 2 and is used cyclically without waste.

Further, in order to improve sealing performance, an O ring 32 is disposed between the annular flange 31 and the corresponding essential oil bottle 2.

In this embodiment, as shown in FIG. 1 and FIG. 3, the lower end of the gasification chamber body 4 comprises a first thread, and the open end of the corresponding essential oil bottle 2 comprises a corresponding second thread. Specifically, an internal thread is disposed on a lower end of the gasification chamber body 4, and a corresponding external thread is disposed on an open end of the corresponding essential oil bottle 2, and the first thread is connected to the second thread. The sealing performance is good. It makes for dismounting of the essential oil bottle 2 and charging of liquid essential oil.

In this embodiment, in order to improve sealing performance, a seal ring is disposed between the oil conduit 8 and the essential oil nozzle 7.

In this embodiment, as shown in FIG. 5 and FIG. 6, a pump cover 33 is disposed at the lower end of the pump mounting rack 19. It can guarantee the working performance and sealing performance of the pump body and is not easily damaged.

In this embodiment, as shown in FIG. 1 and FIG. 3, the upper end of the gasification chamber cover 10 comprises a cover groove 34, the bottom surface of the cover groove 34 comprises a fragrance outlet 12, the fragrance outlet 12 fits with the lower end of the fragrance inlet 18, and the fragrance outlet 12 communicates with the gasification chamber 5 and the fragrance inlet 18.

As shown in FIG. 1 and FIG. 2, in this embodiment, this aroma diffuser has three essential oil bottles 2. Accordingly, the numbers of the gasification elements and the first grooves 26, the second grooves 27, the fragrance inlets 18, the fragrance access passages 17 and the pump flow regulating buttons 36 on the pump element support plate 25 are all three. After the three essential oil bottles 2 are connected to the corresponding gasification elements, they are placed in the corresponding first grooves 26 and second grooves 27. The holder 22 of each of the pump elements is disposed on a lower end of the first groove 26 receiving the corresponding gasification element. The holders 22 of the three pump elements are integral. An upper end of the air output nozzle 23 of each pump element passes through the first groove 26, is inlaid in the air inlet 39 and stretches into the air chamber 6. Three different liquid essential oils are put into three essential oil bottles 2. The three pump flow regulating buttons 36 and time setting buttons 37 are regulated and set according to the actually needed optimum mixing proportion and working time of the essential oil. The power switch 38 is on. The three pump bodies 20 output corresponding air flow under action of the control panel 35. The air flow is output into the air chamber 6 via the air duct 21, the mounting hole 24 and the air output nozzle 23 in turn. The airstream in the air chamber 6 is sprayed out from the air nozzle 9 at a high speed and forms negative pressure above the essential oil nozzle 7. At the moment, the oil conduit 8 sucks the liquid essential oil out from the essential oil bottle 2 and sprays it out from the gasification chamber 5 through the essential oil nozzle 7. Meanwhile, the jet stream sprayed out from the air nozzle 9 gasifies the liquid essential oil sprayed out from the essential oil nozzle 7 into tiny particles, which will become essential oil gas. When essential oil gas collides with the inner wall of the gasification chamber 5, part of it will become liquid essential oil and flow back to the essential oil bottle 2, while the remaining essential oil gas will be discharged from the fragrance outlet 12 under action of the lower vortex body 28 and the upper vortex body 29. Three kinds of essential oil gases enter three fragrance access passages 17 via three fragrance inlets 18. When the essential oil gases in the three fragrance access passages 17 arrive at the mixing chamber, they rotate in the spiral channel set by the mixing blade 14 and are mixed. After mixing, the gases are diffused to the air from the centralized fragrance diffusion outlet 3 via the fragrance converging port 16, thereby completing the process of aroma diffusion, i.e.: achieving the needed effect of compound essential oil after mixing.

The present invention further discloses an aroma diffusing method, comprising:

Providing an aroma diffuser, comprising: a housing 1, at least two essential oil bottles 2, gasification elements, pump elements, a fragrance mixing element and an electric control element.

Under action of the electric control element, importing ambient air into air chambers 6 of the gasification elements through pump bodies 20 of the pump elements and forming jet stream Spraying the jet stream above an essential oil nozzle 7 of each of the gasification elements to form negative pressure so as to suck liquid essential oil out from the respective essential oil bottles 2 and gasify the liquid essential oil into essential oil gas.

Mixing the essential oil gas, and diffusing the mixed essential oil gas to ambient air through a centralized fragrance diffusion outlet 3 of the housing 1.

Further comprising: regulating flow and working time of each pump body 20 of the pump elements according to actual need to achieve the required essential oil mixing proportion and working time.

Further comprising: collecting the essential oil gas which becomes liquid essential oil when it collides with inner walls of the gasification chambers 5 of the respective gasification elements back to the respective essential oil bottles 2.

Further, the fragrance mixing element comprises a mixing blade with a spiral channel 14, the gasified essential oil gases rotate and are mixed in the spiral channel after the gasified essential oil gases are imported to the mixing chamber of the fragrance mixing element.

Further comprising: forming the gasified essential oil gases into vortex airstreams through lower vortex bodies 28 and upper vortex bodies 29 of the gasification elements and importing the airstreams into the mixing chamber of the fragrance mixing element for mixing Further, the lower vortex bodies 28 and the upper vortex bodies 29 form spiral channels. When essential oil gases pass the spiral channels, the essential oil gases in large particle size are blocked, flow back into the gasification chambers 5 and return to the essential oil bottles 2 along inner walls of the gasification chambers 5, while the essential oil gases in small particle size are imported to the mixing chamber of the fragrance mixing element for mixing.

During use of the aroma diffuser with an adjustable essential oil gas proportion disclosed by the present invention, and implementation of the aroma diffusing method, the following steps may be referred to:

A. Separately charging different liquid essential oils into the essential oil bottles 2;

B. Calculating the optimum mixing proportion and working time of each essential oil according to the actual environmental need and the characteristics of the essential oils (an optional step);

C. Adjusting the pump flow regulating button 36 and the time setting button 37 according to the mixing proportion and working time in step B;

D. Starting the power switch 38 after setting. Under action of the pump elements, the gasification elements and the fragrance mixing element, the effect of a compound essential oil may be achieved by mixing essential oils according to the proportion in the set working time.

Embodiment 1

A method for use the aroma diffuser with an adjustable essential oil gas proportion, comprising:

A. Putting peppermint, lavender and cedar liquid essential oils into three essential oil bottles 2 separately;

B. Calculating the optimum mixing proportion of peppermint, lavender and cedar essential oils 35%, 35%, 25% and the optimum working time 2 h in a space of 50 square meters according to the characteristics of peppermint, lavender and cedar essential oils;

C. Adjusting the pump flow regulating button 36 and the time setting button 37 according to the mixing proportion and working time in step B;

D. Starting power switch 38 after setting. Under action of the pump elements, the gasification elements and the fragrance mixing element, the effect of a compound essential oil may be achieved in 2 h by mixing peppermint, lavender and cedar essential oils in a proportion of 35%, 35% and 25%.

Embodiment 2

A method for use the aroma diffuser with an adjustable essential oil gas proportion, comprising:

A. Putting peppermint and cedar liquid essential oils in two essential oil bottles 2 separately;

B. Calculating the optimum mixing proportion of peppermint and cedar essential oils 35%, 25% and the optimum working time 2 h in a space of 50 square meters according to the characteristics of peppermint and cedar essential oils;

C. Adjusting the pump flow regulating button 36 and the time setting button 37 according to the mixing proportion and working time in step B;

D. Starting power switch 38 after setting. Under action of the pump elements, the gasification elements and the fragrance mixing element, the effect of a compound essential oil may be achieved in 2 h by mixing peppermint and cedar essential oils in a proportion of 35% and 25%.

The foregoing embodiments only represent the preferred embodiments of the present invention. Their descriptions are concrete and detailed, but they shall not be therefore understood as limitations to the scope of the present invention patent. It shall be noted that for those skilled in the art, various changes and modifications may be made to the embodiments without departing from the spirit of the present invention, such as: combinations of different features of the embodiments. All these shall be in the protective scope of the present invention.

What is claimed is:

1. An aroma diffuser with an adjustable essential oil gas proportion, comprising a housing and an electric control element on the housing, wherein inside the housing there are at least two essential oil bottles, gasification elements corresponding to the essential oil bottles, pump elements corresponding to the gasification elements and a fragrance mixing element; a lower end of each of the gasification elements being connected to an open end of the corresponding essential oil bottle, each of the gasification elements communicating with the open end of the corresponding essential oil bottle, and an upper end of each of the gasification elements stretching into a cavity at a lower end of the fragrance mixing element and fitting with an end face of the cavity; the lower end of the fragrance mixing element communicating with the upper end of each of the gasification elements, an upper end of the fragrance mixing element communicating with a centralized fragrance diffusion outlet; each of the pump elements being connected to the corresponding gasification element and the electric control element, each of the pump elements communicating with the corresponding gasification element.

2. The aroma diffuser according to claim 1, wherein inside the housing there is a support plate; the support plate comprising first grooves corresponding to all the gasification elements, the gasification elements being placed inside the first grooves, bottom surfaces of the first grooves comprising second grooves, the essential oil bottles connected to the lower ends of the gasification elements being placed inside the second grooves.

3. The aroma diffuser according to claim 2, wherein each of the gasification elements comprises a gasification chamber body; a lower end of the gasification chamber body being connected to the open end of the corresponding essential oil bottle; the gasification chamber body comprising a gasification chamber, an air chamber, and an essential oil nozzle, an air inlet and an oil conduit disposed at the lower end of the gasification chamber body; the gasification chamber communicating with the air chamber through an air nozzle, an upper end of the essential oil nozzle stretching into the gasification chamber and being close to the air nozzle, the gasification chamber communicating with the essential oil nozzle and the open end of the corresponding essential oil bottle respectively; the air inlet communicating with the air chamber; the oil conduit being disposed at a lower end of the essential oil nozzle, the oil conduit communicating with the essential oil nozzle, an lower end of the oil conduit stretching into the corresponding essential oil bottle; surface of the lower end of the oil conduit being close to bottom surface of the essential oil bottle, and being a slope.

4. The aroma diffuser according to claim 3, wherein each of the gasification elements further comprises a gasification chamber cover; the gasification chamber cover being snapped into the gasification chamber body, an upper end of the gasification chamber cover stretching into the cavity at the lower end of the fragrance mixing element and fitting with an end face of the cavity, the upper end of the gasification chamber cover comprising a fragrance outlet, the fragrance outlet communicating with the gasification chamber and the lower end of the fragrance mixing element.

5. The aroma diffuser according to claim 4, wherein the fragrance mixing element comprises a mixing chamber cover, a mixing blade and a mixing chamber base; the mixing chamber cover being snapped into the mixing chamber base, the mixing blade being snapped into the mixing chamber base and contained in a mixing chamber enclosed by the mixing chamber cover and the mixing chamber base, and the mixing chamber base being disposed on the support plate; an upper end of the mixing chamber cover comprising a fragrance converging port, the fragrance converging port being inlaid in the centralized fragrance diffusion outlet at an upper end of the housing, and the fragrance converging port communicating with the centralized fragrance diffusion outlet and the mixing chamber respectively; an upper end of the mixing chamber base comprising fragrance access passages corresponding to each of the gasification elements, the fragrance access passages communicating with the mixing chamber, a lower end of the mixing chamber base having a cavity, enclosing the first groove to underneath of the cavity, an upper end of the gasification chamber cover stretching into the cavity and fitting with an end face of the cavity, and a fragrance inlet communicating with the fragrance outlet and the fragrance access passage being on the end face of the cavity.

6. The aroma diffuser according to claim 5, wherein each of the pump elements comprises a pump mounting rack disposed inside the housing, a pump body disposed inside the pump mounting rack, an air duct, a holder and an air output nozzle; the holder being disposed on a lower end of the first groove receiving the corresponding gasification element and the holder comprising a mounting hole; one end of the air duct being connected to the pump body, another end of the air duct sticking out from an upper end of the pump mounting rack and being fixed onto the mounting hole, and the air duct communicating with the mounting hole; a lower end of the air output nozzle being fixed onto the mounting hole; an upper end of the air output nozzle passing through the first groove, being inlaid in the air inlet and stretching into the air chamber, and the air output nozzle communicating with the air chamber and the mounting hole respectively.

7. The aroma diffuser according to claim 6, wherein the gasification chamber body further comprises a lower vortex body and an upper vortex body; the lower vortex body and the upper vortex body being disposed inside the gasification chamber from bottom to top in turn, a lower end of the upper vortex body being connected to the lower vortex body, an upper end of the upper vortex body being connected to the gasification chamber cover, the upper vortex body, the lower vortex body and the gasification chamber being mutually communicable.

8. The aroma diffuser according to claim 1, wherein the electric control element comprises a control panel, a pump flow regulating button corresponding to each pump element, a time setting button and a power switch; the pump flow regulating button, the time setting button and the power switch being all connected to the control panel, and the control panel being connected to all pump elements.

9. The aroma diffuser according to claim 3, wherein the gasification chamber body further comprises a pressure plunger; the pressure plunger being disposed on a side face of the gasification chamber body, one end of the pressure plunger being inside the air chamber, and the pressure plunger being on opposite of the air nozzle.

10. The aroma diffuser according to claim 3, wherein bottom surface of the gasification chamber comprises an annular flange inlaid in the open end of the corresponding essential oil bottle.

11. The aroma diffuser according to claim 10, wherein an O ring is disposed between the annular flange and the corresponding essential oil bottle.

12. The aroma diffuser according to claim 3, wherein the lower end of the gasification chamber body comprises a first thread, the open end of the corresponding essential oil bottle comprising a corresponding second thread, the first thread being connected to the second thread.

13. The aroma diffuser according to claim 3, wherein a seal ring is disposed between the oil conduit and a lower end of the essential oil nozzle.

14. The aroma diffuser according to claim 6, wherein a pump cover is disposed at a lower end of the pump mounting rack.

15. The aroma diffuser according to claim 5, wherein the upper end of the gasification chamber cover comprises a cover groove; bottom surface of the cover groove comprising a fragrance outlet, the fragrance outlet fitting with a lower end of the fragrance inlet, and the fragrance outlet communicating with the gasification chamber and the fragrance inlet respectively.

16. An aroma diffusing method, comprising:
providing an aroma diffuser comprising a housing, at least two essential oil bottles, gasification elements, pump elements, an fragrance mixing element and an electric control element;
under action of the electric control element, importing ambient air into air chambers of the gasification elements through pump bodies of the pump elements and forming jet stream;
spraying the jet stream above an essential oil nozzle of each of the gasification elements to form negative pressure so as to suck liquid essential oil out from the respective essential oil bottles and gasify the liquid essential oil into essential oil gas;
mixing the essential oil gas;
diffusing the mixed essential oil gas to ambient air through a centralized fragrance diffusion outlet of the housing.

17. The aroma diffusing method according to claim 16, further comprising: regulating flow and working time of each pump body of the pump elements according to actual need to achieve the required essential oil mixing proportion and working time.

18. The aroma diffusing method according to claim 16, further comprising: collecting the essential oil gas which becomes liquid essential oil when it collides with inner walls of the gasification chambers of the respective gasification elements back to the respective essential oil bottles.

19. The aroma diffusing method according to claim 16, wherein the fragrance mixing element comprises a mixing blade with a spiral channel; the gasified essential oil gases rotating and mixing in the spiral channel after the gasified essential oil gases being imported to the mixing chamber of the fragrance mixing element.

20. The aroma diffusing method according to claim 16, further comprising: forming the gasified essential oil gases into vortex airstreams through lower vortex bodies and upper vortex bodies of the gasification elements and importing the airstreams into the mixing chamber of the fragrance mixing element for mixing.

21. The aroma diffusing method according to claim 20, wherein the upper vortex bodies and the lower vortex bodies form spiral channels, when essential oil gases pass the spiral channels, the essential oil gases in large particle size being blocked, flowing back into the gasification chambers and returning to the essential oil bottles along inner walls of the gasification chambers, while the essential oil gases in small particle size being imported to the mixing chamber of the fragrance mixing element for mixing.

\* \* \* \* \*